United States Patent [19]
Akagi et al.

[11] Patent Number: 5,360,725
[45] Date of Patent: Nov. 1, 1994

[54] METHOD OF PRODUCING RICE CYBRID CELLS

[75] Inventors: Hiromori Akagi; Masahiro Sakamoto, both of Yokohama; Tatsuhito Fujimura, Sagamihara, all of Japan

[73] Assignee: Mitsui Toatsu Chemicals, Inc., Tokyo, Japan

[21] Appl. No.: 58,666

[22] Filed: May 10, 1993

Related U.S. Application Data

[63] Continuation of Ser. No. 928,656, Aug. 17, 1992, abandoned, which is a continuation of Ser. No. 630,777, Dec. 21, 1990, abandoned, which is a continuation of Ser. No. 305,511, Feb. 2, 1989, abandoned.

[30] Foreign Application Priority Data

Feb. 2, 1988 [JP] Japan ................... 63-21273

[51] Int. Cl.$^5$ .......................... C12N 5/14; A01H 4/00
[52] U.S. Cl. .................... 435/172.2; 435/240.4; 435/240.47; 435/240.5; 800/220; 800/DIG. 57
[58] Field of Search ............. 435/172.2, 240.4, 240.47, 435/240.48, 240.49, 240.5; 800/220, DIG. 57; 935/91, 92, 94, 95, 98

[56] References Cited

U.S. PATENT DOCUMENTS

| | | | |
|---|---|---|---|
| 4,351,130 | 9/1982 | Rutger et al. | 47/58 |
| 4,677,066 | 6/1987 | Takahashi et al. | 435/172.2 |
| 4,764,643 | 8/1988 | Calub | 47/58 |

FOREIGN PATENT DOCUMENTS 0202667 11/1986 European Pat. Off. ........ 435/240.47

OTHER PUBLICATIONS

Bates 1983) Plant Physiol 72:1110–1113.
Menczel (1983) Mole Gene Genet 189:365–369.
Sidorov (1981) Planta 152:341–345.
Ichikawa (1987) Theor Appl Genet 74:746–752.
Menczel (2987) Plant Cell Report 6:98–101.
Aviv (1980) Theor Appl Genet 58:121–127.
Bates (1987) Theor Appl Genet 74:718–726.
Zelcer (1987) Z Pflanzenphysiol 90:397–407.
Fluhr (1984) Theor Appl Genet 67:491–497.
Medgyesy (1985) Theor Appl Genet 70:590–594.
Cseplo (1984) Mole Gene Genet 198:7–11.
Kemble (1986) Theor Appl Genet 72:787–793.
Fujimura (1985) Plant Tissue Culture Lett 2:74–75.
Barbsy (1987) Plant Sci 53:243–248.
Pelletier (1983) Mole Gen Genet 191:244–252.
Sidorov (1987) Theor Appl Genet 74:364–368.
Robertson (1987) Theor Appl Genet 74:303–309.
Terada (1987) Theor Appl Genet 73:379–384.
Galun (1986) Organelle transfer: Methods in Enzymology, vol. 118. Academic Press, New York, pp. 595–611.
Terada (1987) Mole Gene Gent 210:39–43.
Kumashiro (1986) Japan J Breed 36:39–48.
Jones, "Fusing plant protoplasts," *Tibtach,* Jul. 1988, vol. 6, pp. 153–158.
"Molecular and General Genetics," vol. 215, No. 3, pp. 501–506; H. Akagi et al. Construction of Rice Cybrid Plants.
Theoretical and Applied Genetics, vol. 58, 1980, pp. 121–127, "Restoration of Fertility . . . Protoplats".
P. V. Ammirato et al., "Handbook of Plant Cell Cul- (List continued on next page.)

*Primary Examiner*—Che S. Chereskin
*Attorney, Agent, or Firm*—Birch, Stewart, Kolasch & Birch

[57] ABSTRACT

A method of producing rice cybrid cells includes the steps of irradiating with X-rays to first rice protoplasts containing a first useful gene in the cytoplasm thereof to selectively destroy the nuclei thereof only; treating second rice protoplasts containing a second useful gene in the nucleus thereof with about 10 - 30 mM of iodoacetamide, about 0.1 - 0.5 mM Rhodamine 6G or about 10 - 30 mM iodoacetate to selectively deactivate the cytoplasm; and fusing the treated first and second protoplasts to form cybrid cells which have only the nucleus containing the first useful gene and have only the cytoplasm containing the second useful gene.

25 Claims, 2 Drawing Sheets

OTHER PUBLICATIONS ture," vol. 3 Crop Species; 1984 Macmillan Publishing Co., New York, Chapter 6, pp. 151–170.

"Biotechnology in Agriculture and Forestry 2," Crops I, Bajaj, ed., Springer-Verlag, Berlin; Chapter I.6, pp. 105–122; Maeda et al., Rice: Regeneration of Plants from Callus Cultures.

Potrykus et al. (1987) in Plant Gene Research: Plant DNA infectious agents, Springer-Verlag, pp. 229, 240.

Yang, et al. (Dec. 30, 1988) Theor. Appl. Genet. 76: 801–808.

Kyozuka, et al. (Apr. 1988) Theor. Appl. Genet. 76: 887–890.

Zimmermann, et al. (1981) Planta 151: 26–32.

Morgan, et al. (1987) Mol. Gen. Genet. 209: 240–246.

Solun, et al (1986) Methods in Enzymology 118: 595–611.

METHOD OF PRODUCING RICE CYBRID CELLS

This application is a continuation, of application Ser. No. 07/928,656 filed on Aug. 17, 1992, now abandoned, which is a continuation of application Ser. No. 07/630,777 filed on Dec. 21, 1990, now abandoned which is a continuation of application Ser. No. 07/305,511 filed on Feb. 2, 1989, also now abandoned.

BACKGROUND OF THE INVENTION

I. Field of the Invention

This invention relates to a method of producing rice cybrid cells and plants. This invention is useful in the breeding of rice.

II. Description of the Related Art

In recent years, a number of methods have been reported in which a whole plant is regenerated from a cell prepared by cell fusion. By these methods, the hybridization of plants of distant relation can be attained, which was hitherto impossible. In addition, the combination or exchange of the cytoplasm of the parents (cybridization), which was hitherto impossible in the conventional hybridization breeding technique, can be attained by these methods.

Unlike the conventional backcross breeding which requires a long period of time, cybridization can be carried out in a short period of time, so that the cybridization technique is now intensively studied in the field of breeding of plants.

However, up to now, cybrids were successfully provided in a limited number of plant species, such as the tobacco, carrot and potato species.

Rice is an important crop and rice plants with improved characteristics are desired. Up to now, however, a cybrid of rice or even a somatic hybrid of rice has not yet been obtained.

SUMMARY OF THE INVENTION

Accordingly, the object of the present invention is to provide a method of producing rice cybrid cells and plants.

In general, to provide a cybrid, at least three problems should be solved. That is, 1) the conditions for destroying the nuclei of parent protoplasts, 2) the conditions for inactivating the cytoplasm of one of the parent protoplasts, and 3) the conditions for fusing both the parent protoplasts should be selected. These conditions are unique for each plant species, so that these conditions are needed to be appropriately selected for each plant species.

The present inventors have intensively studied these problems in order to find these conditions for rice such that the nuclei of rice protoplasts can be destroyed without damaging the viability of the protoplasts by irradiation with X-rays, such that the cytoplasm of rice protoplasts can be inactivated without damaging the viability of the protoplasts by treating the protoplasts with a specific reagent, and such that the thus treated protoplasts can be fused to provide cybrid rice cells, thereby completing the present invention.

That is, the present invention provides a method of producing rice cybrid cells comprising the steps of irradiating with X-rays to first rice protoplasts containing a first useful gene in the cytoplasm thereof to selectively destroy the nuclei only; treating the nuclei of second rice protoplasts containing a second useful gene with iodoacetate, Rhodamine 6G or iodoacetage to selectively inactivate the cytoplasm; and fusing the treated first and second protoplasts to form cybrid cells which have only the cytoplasm containing the first useful gene and have only the nuclei containing the second useful gene.

By the present invention, a method by which rice cybrid cells can be obtained was first provided. By virtue of the present invention, rice plants with improved characteristics may be bred in a short period of time without employing the conventional backcross breeding which requires a long period of time.

DETAILED DESCRIPTION OF THE PREFERRED EMBODIMENTS

Figure 1:
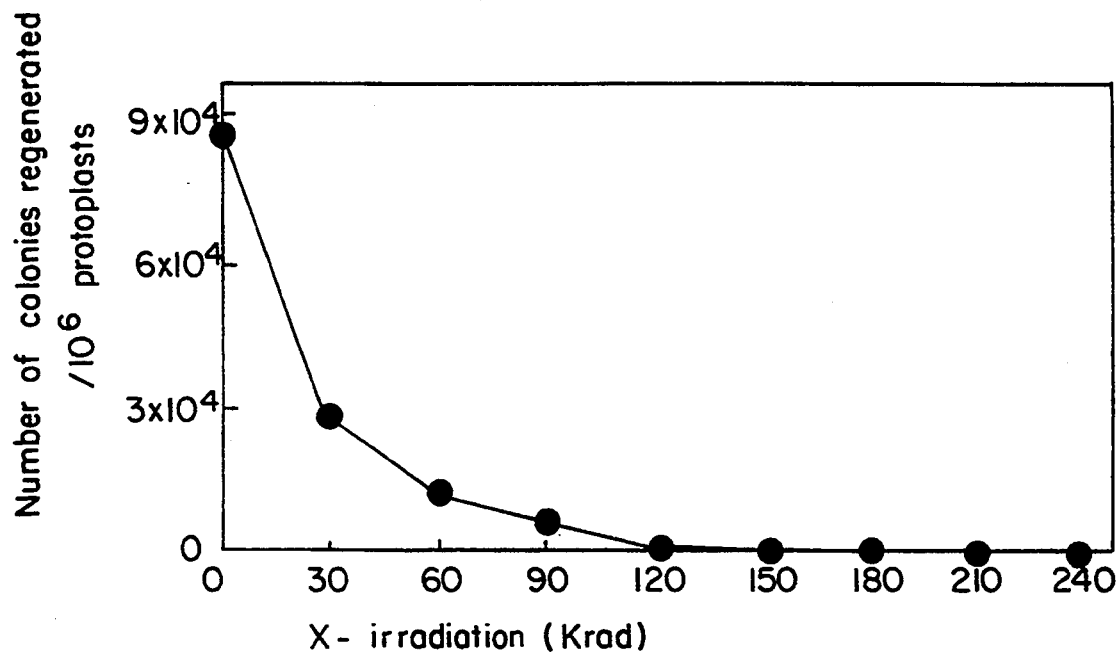
FIG. 1 shows the relationship between the dose of x-ray irradiation given to rice protoplasts and the number of the colonies regenerated from the irradiated protoplasts.

The term "cybrid cell" herein means the fusion product of another portion of protoplast (subprotoplast) and a subprotoplast or a whole protoplast.

As described above, the method of the present invention includes the steps of selectively destructing the nuclei of first protoplasts, selectively inactivating the cytoplasm of second protoplasts, and fusion of the thus treated first and second protoplasts. These steps will now be described in detail separately.

I. Destruction of Nuclei

In the method of the present invention, the nuclei of first rice protoplasts which have a useful gene in the cytoplasm are destroyed by irradiating with X-rays to the rice protoplasts. Rice protoplasts per se may be prepared by the conventional method well-known in the art (e.g., Fujimura et al., Plant Tissue Culture Letters, 2(2): 74–75). The useful gene contained in the cytoplasm of the first protoplasts may be, for example, male sterility factor. It is necessary, by this step, to provide subprotoplasts in which the nuclei are destroyed while the normal cytoplasm is retained. In a preferred mode, this may be accomplished by irradiating with X-rays to rice protoplasts placed in a suspension, for example, in a Petri dish with a population density of not more than $10^8$/ml, preferably $10^6$ - $4 \times 10^7$/ml. Soft X-ray treatment is preferred as the X-ray treatment. The dose of the X-ray is preferably 90–250 krad for the protoplasts, more preferably 120–150 krad. This dosage may be attained, for example, by applying power with a voltage of 20–200 kV and a current of 3–20 mA to a commercially available X-ray tube. By this operation, rice subprotoplasts which maintain their physiological properties for a certain period of time while their cell division is inhibited may be obtained.

II. Inactivation of Cytoplasm

In this step, second rice protoplasts containing a useful gene in the nuclei are treated with iodoacetamide, Rhodamine 6G or with iodoacetate to inactivate the cytoplasm of the protoplasts. The useful gene contained in the nuclei may be, for example, a gene providing a good taste to the rice grain, a gene providing cold resistance to the plant and/or a gene providing high yield of the plant. Inactivation of the cytoplasm herein means destroying organella or inactivating replication of organella in cytoplasm. In a preferred mode, the treatment may be conducted by suspending protoplasts in an hypertonic solution such as a glucose solution with a concentration of 0.3–0.5 M containing iodoacetamide, Rhodamine 6G or iodoacetate. The concentration of iodoacetamide or iodoacetate in the solution is about 10–30 mM. The concentration of Rhodamine 6G in the solution is about 0.1–0.5 mM. In an preferred mode, to obtain only the desired cybrid, the protoplasts are treated with 16–30 mM iodoacetamide, more preferably with 25–30 mM iodoacetamide. The treatment may preferably be conducted for 10 minutes to 30 minutes at 4° C. to 30° C. The population density of the protoplasts in the suspension is preferably not more than $10^8$/ml, more preferably $10^6$ - $4 \times 10^7$/ml. After the treatment, the protoplasts are washed with the same solution but not containing iodoacetamide, Rhodamine 6G or iodoacetate. Since the washing of the protoplasts is usually conducted by centrifugation, it is convenient to suspend the protoplasts in a centrifugation tube. The washing is usually conducted several times, for example, four times.

By this operation, protoplasts having normal nuclei and inactivated cytoplasm are obtained. Although the cytoplasm of the protoplasts is inactivated, the thus treated protoplasts still retain the ability to be fused with other protoplasts.

III. Cell Fusion

In this step, the protoplasts having nuclei which were destroyed as described in I, and the protoplasts having cytoplasm which was inactivated as described in II are fused. The cell fusion may be attained based on the known polyethylene glycol method or electro fusion method (EF method). More specifically, in a preferred mode, the cell fusion may be attained by the following methods:

1) Polyethyleneglycol method

The X-ray treated protoplasts as described in I and the protoplasts treated as described in II are mixed. This can be accomplished by mixing suspensions of the protoplasts. In each suspension, the population density of the protoplasts is preferably $10^6$–$2 \times 10^7$/ml. Further, the number ratio of the X-ray-treated protoplasts to the reagent-treated protoplasts is preferably 1:1 to 5:1. To the resulting mixed suspension of protoplasts, polyethyleneglycol having an average molecular weight of preferably 1500–9000 and a concentration of preferably 20–50% by weight) is added. The volume of the polyethyleneglycol may preferably be about the same volume as the suspension. The resulting mixture is then left to stand, for example, 5–15 minutes at room temperature. Thereafter, the polyethyleneglycol is removed by centrifugation and the fused protoplasts are washed, for example, three times by centrifugation with glucose solution at a concentration of, for example, 0.4 M.

2) Electrofusion method

The X-ray treated protoplasts as described in I and the protoplasts treated as described in II are mixed in the same manner as in polyethyleneglycol method described above. The mixed suspension is then placed between a pair of parallel electrodes in a cell fusion apparatus. The protoplasts are then electrically stimulated by applying the following electric stimulation i) to iii) in the order mentioned:

i) high frequency of 0.75–2.0 MHz, 120–200 V/cm for 3–10 seconds, ii) high frequency of 0.75–2.0 MHz, 200–400 V/cm for 0.1–0.3 seconds, and iii) rectangular or attenuated wave of 2000 to 3500 V/cm for 10–300 microseconds, 1–3 times. After applying the electric voltage of i) to iii), the suspension of protoplasts is then left to stand for usually 15 to 20 minutes at room temperature, followed by washing.

By the above-described steps, rice cybrid cells may be obtained. By checking the protoplasts after the above-described fusion operation by staining the protoplasts with two kinds of fluorescent dyes, i.e., fluorescein isothiocyanate and rhodamineisothiocyanate, it was confirmed that about 30% of the protoplasts formed cybrid cells in either of the polyethyleneglycol method or EF method.

From the thus prepared cybrid cells, whole rice plants can be regenerated. The regeneration of whole plants from cybrid cells may be conducted in the same manner as the regeneration of whole plants from normal protoplasts. The method of regenerating whole plants from protoplasts has been established and is described in Fujimura et al (supra) which is hereby incorporated by reference, and in copending U.S. patent application No. 06/865,519 and corresponding EPC patent application No. 0202,667 Canadian patent application No. 509,543 and Chinese patent application No. 86103448. The regenerated rice plants may be grown in a green house after conventional acclimatization.

The invention will now be described by way of examples thereof. The examples are presented for the purpose of illustration only and should not be interpreted in any restrictive way.

EXAMPLE 1

In accordance with the method described in Fujimura et al (1985, supra), protoplasts were isolated from the suspended cell culture of rice (variety: Sasanishiki which is famous for its delicious taste). The protoplasts, were irradiated with various doseages of x-rays. The irradiated protoplasts were cultured in accordance with Fujimura et al (1985, supra). After 14 days from the irradiation, the number of colonies regenerated was checked. The results are shown in FIG. 1. In FIG. 1, the abscissa indicates the total dosage of the X-ray and the ordinate indicates the number of colonies regenerated within 14 days from the irradiation of X-ray.

The were irradiated with x-rays protoplasts as follows: Protoplasts were suspended in an enzymatic solution (4% by weight of cellulase onozuka RS(Yakult Honsha Co., Ltd), 1% by weight of Macerozyme R-10 (Yakult Honsha Co., Ltd), 0.5% by weight of potassium dextran sulfate (Meito Sangyou Co., Ltd), 0.5% by weight of calcium chloride dihydrate and 0.4 M of mannitol (pH 5.5) to a population density of $2 \times 10^7$/ml so as to inhibit the regeneration of the cell wall. Two milliliters of the suspension was placed in a Petri dish of 60 mm diameter and the suspension was irradiated with x-rays. The X-rays were generated by applying a power of 100 kV, 4 mA to an X-ray tube. The dosage of X-rays was varied by changing the duration of the irradiation. The dosage per minute was 2 krad.

By this experiment, it was proven that in order to inhibit the cell division of rice protoplasts, it is necessary to irradiate the protoplasts with X-rays of not less than 90 krad, preferably not less than 120 krad, which is much greater than that required for tobacco (15 krad) or for carrot (60 krad) plants.

On the other hand, by observing the protoplasts irradiated with X-rays using a microscope, active protoplasmic streaming was observed until one day after the irradiation when the dosage of X-rays was not more than 250 krad, or until five days after the irradiation when the dosage of X-rays was not more than 150 krad.

From this observation, it can be seen that if the rice protoplasts are irradiated with X-ray at a dosage of 90–250 krad, preferably 120–150 krad, although the cell division is inhibited, the physiological activity of the protoplasts is retained at a comparatively high level for a certain period of time.

From these observations, it was proven that the subprotoplasts having nuclei which are destroyed as mentioned above are suitable as a parent for the preparation of a rice cybrid.

EXAMPLE 2

In accordance with the method described in Fujimura et al (1985 supra) protoplasts were isolated from the suspended cell culture of rice (variety: Sasanishiki). The protoplasts were suspended at a population density of $2 \times 10^7$/ml in 0 4 M of glucose containing various amounts of iodoacetamide at 25° C. for 15 minutes. After this I treatment, the protoplasts were washed four times with 0.4 M glucose solution.

Figure 2:
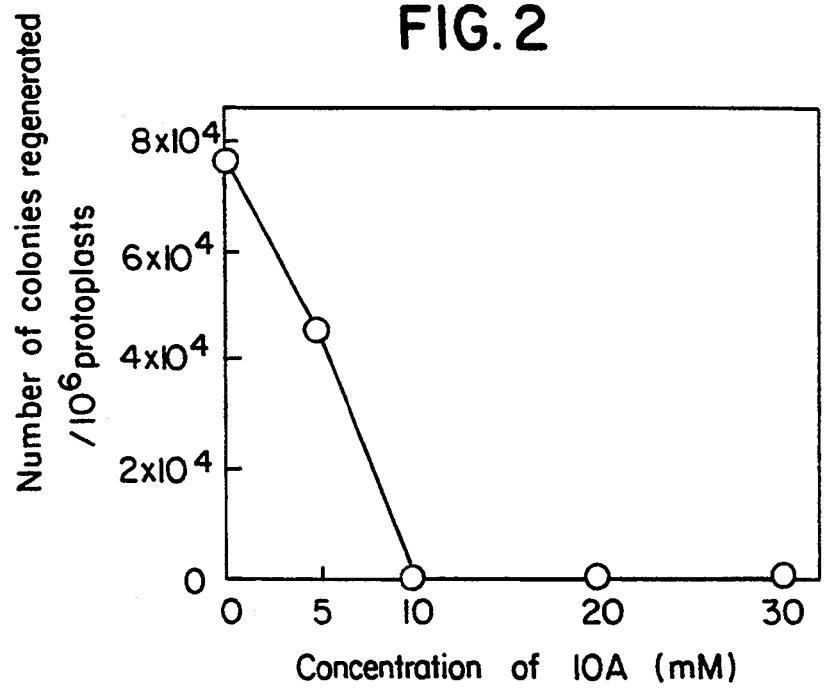
FIG. 2 shows the relationship between the concentration of iodoacetamide with which the rice protoplasts were treated and the number of the colonies regenerated from the irradiated protoplasts.

The thus treated protoplasts were cultured in accordance with the method described in Fujimura et al (1985, supra). After 14 days from the treatment, the number of regenerated colonies was checked. The results are shown in FIG. 2. In FIG. 2, the abscissa indicates the concentration of the iodoacetamide and the ordinate indicates the number of regenerated colonies.

By this experiment, it was shown that it is necessary to treat the rice protoplasts with iodoacetate at a concentration of not less than 10 mM, which is much higher than that required for tobacco or potato plants.

On the other hand, the treated protoplasts were observed with a microscope. By this observation, it was shown that when the protoplasts were treated with iodoacetate at a concentration of 10–30 mM, the cell division was inhibited while the protoplasts retained the normal cell structure until at least two days after the treatment and also retained their physiological activity indicated by dying the protoplasts with fluorescein diacetate (FDA). If the protoplasts were treated with iodoacetate at a concentration of not less than 35 mM, the protoplasts were destroyed during the treatment.

From these observations, it was proven that the rice subprotoplasts in which cell division is inhibited which are viable for a certain period of time, which are obtained by treating the protoplasts with iodoacetamide at a concentration of 10–30 mM, preferably 16–30 mM, more preferably 25–30 mM and are suitable as a parent for preparing a rice cybrid.

EXAMPLE 3

In accordance with the method described in Fujimura et al (1985, supra), protoplasts were isolated from the suspended cell culture of rice (variety: Sasanishiki). The protoplasts were suspended at a population density of $2 \times 10^7$/ml in 0.4 M of glucose containing various amounts of Rhodamine 6G at 25° C. for 15 minutes. After this treatment, the protoplasts were washed four times with 0.4 M glucose solution.

Figure 3:
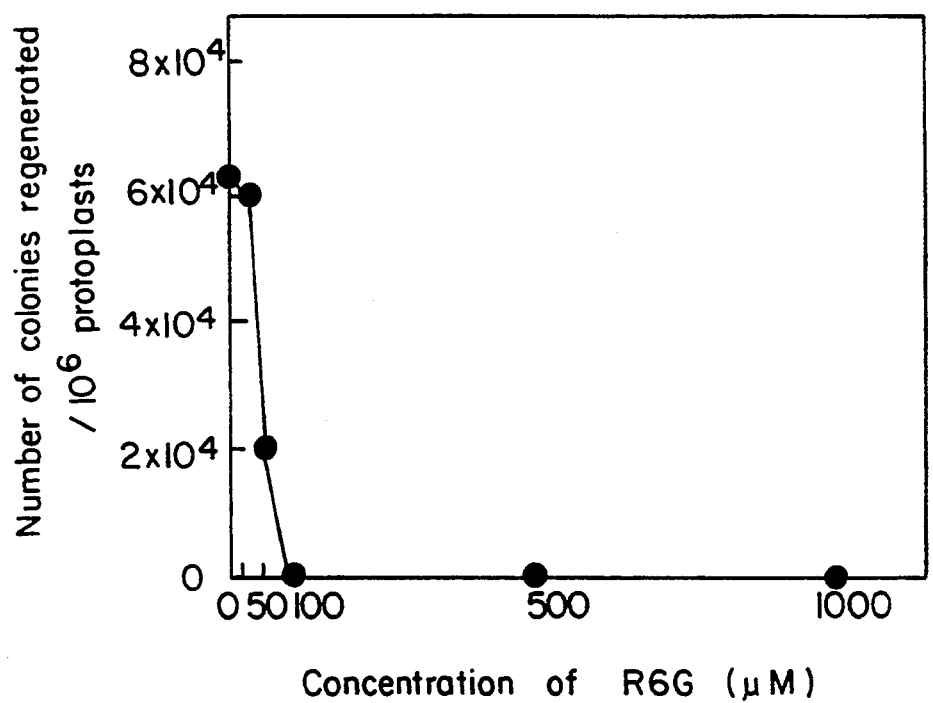
FIG. 3 shows the relationship between the concentration of Rhodamine 6G with which the rice protoplasts were treated and the number of the colonies regenerated from the irradiated protoplasts.

The thus treated protoplasts were cultured in accordance with the method described in Fujimura et al (1985, supra). After 14 days from the treatment, the number of regenerated colonies was checked. The results are shown in FIG. 3. In FIG. 3, the abscissa indicates the concentration of the Rhodamine 6G and the ordinate indicates the number of regenerated colonies.

By this experiment, it was shown that it is necessary to treat the rice protoplasts with Rhodamine 6G at a concentration of not less than 0.1 mM.

On the other hand, the treated protoplasts were observed with a microscope. By this observation, it was shown that when the protoplasts were treated with Rhodamine 6G at a concentration of 0.1–0.5 mM, the cell division was inhibited while the protoplasts retained the normal cell structure until at least two days after the treatment and also retained their physiological activity as indicated by dying the protoplasts with fluorescein diacetate (FDA). If the protoplasts were treated at Rhodamine 6G with a concentration of not less than 1 mM, the protoplasts were destroyed in the treatment.

From these observations, it was proven that the rice subprotoplasts in which cell division is inhibited are viable for a certain period of time, and are obtained by treating the protoplasts with Rhodamine 6G at a concentration of 0.1–0.5 mM and are suitable as a parent for preparing a rice cybrid.

EXAMPLE 4

In accordance with the method described in Fujimura et al (1985, supra), protoplasts were isolated from the suspended cell culture of rice (variety: MT-CMA5) which has been confirmed to have cytoplasmic male sterility factor of Chinsura Boro II type by the electrophoresis pattern of mitochondria DNA (K. Kadowaki et al., Japan J. Breed., 36, 333–339, (1986)). The protoplasts were treated with X-rays at a dosage of 125 krad in the manner as described in Example 1 to obtain subprotoplasts having nuclei which were destroyed.

On the other hand, in accordance with the method described in Fujimura et al (1985, supra), protoplasts were isolated from a suspended cell culture of rice (variety: Sasanishiki). The protoplasts were treated with 30 mM of iodoacetamide at 25° C. for 15 minutes to obtain subprotoplasts which no longer had the ability to divide.

The thus obtained MT-CMA5 subprotoplasts and Sasanishiki subprotoplasts were separately suspended in 0.4 M glucose at a population density of $2 \times 10^7$/ml. The thus obtained suspensions were mixed at a ratio of 1:1. The mixed suspension was placed between a pair of parallel electrodes of a cell fusion apparatus and power was applied across the electrodes as follows in the order mentioned:

1) high frequency of 1 MHz, 150 V/cm for 5 seconds,
2) high frequency of 1 MHz, 250 V/cm for 0.1 second, and
3) rectangular wave of 2500 V/cm for 50 microseconds.

After this electric treatment, the suspension was left to stand at 4° C. for 15 minutes and the cells were washed once with 0.4 M glucose solution. The resulting protoplasts were cultured in a medium with a composition of R2 salts (Ohira, K., K. Ojima, A. Fujiwara, 1973, Plant Cell Physiol., 14:1113-1121), B5 vitamins (Gamborg, OIL., R. A. Miller, K. Ojima, 1968, Expt. Cell Res., 50:151-158), 0.4 M of sucrose and 1 ppm of 2,4-D (2,4-dichlorophenoxyacetic acid) (pH 4.5 ) at 27° C. as described in Fujimura et al (1985 supra).

In two weeks from the beginning of the culture, cell clusters were formed. The cell clusters were transferred to a growth medium with a composition of R2 salts, B5 vitamins, 0.2 M of glucose, 1 ppm of 2,4-D and 0.25 ppm of BA (6-benzyladenine) (pH 5.0) and cultured for two weeks in the growth medium at 27° C. The cell clusters were then transferred to a differentiation medium with a composition of N6 salts (Chu, C.-C., 1978, In "Proceeding of Symposium on Plant Tissue Culture, p 43-50, Scientific Press, Peking.), B5 vitamins, 3% by weight of sucrose, 1 ppm of NAA (naphthaleneacetic acid), 2 ppm of BA and 1% of agar (pH 5.5) and cultured for two weeks at 27° C. to regenerate whole rice plants. The plants were then acclimatized and were grown in a green house to mature. At the time of flowering, self-pollination and cross-pollination were performed to form the rice grains.

By checking the thus regenerated rice plants, the plants were clearly "Sasanishiki" in view of the outer appearance of the plants and the quality of the rice grains after pollinated with original "Sasanishiki". However, the fertility of the pollen was lost. The type of the male sterility was checked by electrophoresis pattern of mitochondria DNA. As a result, it was proved that the mitochondria apparently originated from "MT-CMA5". These results clearly show that the regenerated rice plants were cybrid rice plants which had nuclei of "Sasanishiki" and simultaneously had the cytoplasm of "MT-CMA5".

EXAMPLE 5

In accordance with the method described in Fujimura et al (1985, supra), protoplasts were isolated from the suspended cell culture of rice (variety: MT-CMA9) which has been confirmed to have cytoplasmic male sterility factor of WA type by the electrophoresis pattern of mitochondria DNA (K. Mignouna et al., Theor. Appl. Genet., 74: 666–669 (1987)). The protoplasts were treated with X-rays at a dosage of 150 krad in the manner as described in Example 1 to obtain subprotoplasts having nuclei which were destroyed.

On the other hand, in accordance with the method described in Fujimura et al (1985, supra), protoplasts were isolated from the suspended cell culture of rice (variety: Nihonbare). The protoplasts were treated with 25 mM of iodoacetamide at 25° C. for 15 minutes to obtain subprotoplasts which no longer had the ability to divide.

The thus obtained MT-CMA9 subprotoplasts and Sasanishiki subprotoplasts were separately suspended in 0.4 M glucose at a population density of $2 \times 10^7$/ml. The thus obtained suspensions were mixed at a ratio of 1:1. To the mixed suspension, equal volumes of 40 wt% polyethyleneglycol solution (average molecular weight of 7800–9000) was added and the resulting mixture was left to stand for 15 minutes. The cells were then washed three times with 0.4 M glucose solution.

From the thus obtained fused cells, whole rice plants were regenerated in the manner as in Example 4. The plants were then acclimatized and were grown in a green house to mature. At the time of flowering, self-pollination and cross-pollination were performed to form the rice grains.

By checking the thus regenerated rice plants, the plants were clearly "Nihonbare" in view of the outer appearance of the plants and the quality of the rice grains after pollination with original Nihonbare. However, the fertility of the pollen was lost. The type of the male sterility was checked by inspection of the electrophoresis pattern of the mitochondria DNA. As a result, it was proven that the mitochondria apparently originated from "MT-CMA9". These results clearly show that the regenerated rice plants were cybrid rice plants which had nuclei of "Nihonbare" and simultaneously had the cytoplasm of "MT-CMA9".

We claim:

1. A method of producing rice cybrid cells comprising the steps of:
   (a) irradiating with X-rays at a dosage of 90–250 krad first rice protoplasts containing a first useful gene in the cytoplasm thereof to selectively destroy the nuclei only of the protoplasts;
   (b) treating second rice protoplasts containing a second useful gene in the nuclei thereof with about 10–30 mM of iodoacetamide, about 0.1–0.5 mM of Rhodamine 6G or about 10–30 mM of iodoacetate to selectively deactivate the cytoplasm thereof; and
   (c) fusing the treated first and second protoplasts to form cybrid cells which have only the nuclei containing the first useful gene and have only the cytoplasm containing the second useful gene.

2. The method of claim 1, wherein the X-rays are soft X-rays.

3. The method of claim 1, wherein the dosage of the X-rays is 100–150 krad.

4. The method of claim 1, wherein the second protoplasts are treated in step (b) with iodoacetamide at a concentration of 16–30 mM.

5. The method of claim 1, wherein the treated first and second protoplasts are fused in step (c) using the polyethylene glycol method.

6. The method of claim 1, wherein the treated first and second protoplasts are fused in step (c) using the electrofusion method.

7. The method of claim 1, wherein the number ratio of the treated second protoplasts to the treated first protoplasts is 1:1 to 1:5 when the protoplasts are fused in step (c).

8. The method of claim 1, wherein the second useful gene is a gene for male sterility.

9. A method of producing a rice cybrid plant comprising regenerating a whole plant from the cybrid cell obtained by the method of claim 1.

10. A hybrid rice cell produced by the method of claim 1.

11. The method of claim 1, wherein before irradiation with X-rays in step (a) the first rice protoplasts have a population of from $10^6$ to $4 \times 10^7$/ml.

12. The method of claim 1, wherein the dosage of the X-rays is 120–150 krad.

13. The method of claim 1, wherein the second rice protoplasts are treated in step (b) while being suspended in a glucose solution at a concentration of from 0.3 to 0.5 M.

14. The method of claim 1, wherein the second rice protoplasts are treated in step (b) with about 0.1–0.5 mM Rhodamine 6G.

15. The method of claim 1, wherein the second rice protoplasts are treated in step (b) with about 10–30 mM iodoacetate.

16. The method of claim 1, wherein the second rice protoplasts are treated in step (b) for a time period of about from 10 to 30 minutes at a temperature of from 4° C. to 30° C.

17. A method of producing rice cybrid cells comprising the steps of:
(a) irradiating with X-rays at a dosage of 90–250 krad first rice protoplasts containing a first useful gene in the cytoplasm thereof to selectively destroy the nuclei only of the protoplasts;
(b) treating second rice protoplasts containing a second useful gene in the nuclei thereof with about 10–30 mM of iodoacetamide; and
(c) fusing the treated first and second protoplasts to form cybrid cells which have only the nuclei containing the first useful gene and have only the cytoplasm containing the second useful gene.

18. The method of claim 17, wherein the second protoplasts are treated in step (b) with iodoacetamide at a concentration of 25–30 mM.

19. The method of claim 17, wherein the treated first and second protoplasts are fused in step (c) using the polyethylene glycol method.

20. The method of claim 17, wherein the treated first and second protoplasts are fused in step (c) using the electrofusion method.

21. The method of claim 17, wherein the number ratio of the treated second protoplasts to the treated first protoplasts is 1:1 to 1:5 when the protoplasts are fused in step (c).

22. The method of claim 17, wherein the second useful gene is a gene for male sterility.

23. The method of claim 17, wherein before irradiation with X-rays in step (a) the first rice protoplasts have a population of from $10^6$ to $4 \times 10^7$/ml.

24. The method of claim 17, wherein the dosage of the X-rays is 120–150 krad.

25. The method of claim 17, wherein the second rice protoplasts are treated in step (b) while being suspended in a glucose solution at a concentration of from 0.3 to 0.5 M.

* * * * *